United States Patent
Giba et al.

[11] Patent Number: 5,997,526
[45] Date of Patent: *Dec. 7, 1999

[54] SHAPE MEMORY CATHETER

[75] Inventors: Jeffrey J. Giba, Moreno Valley, Calif.; Gregory P. Walcott, Wilsonville; Raymond E. Ideker, Birmingham, both of Ala.; Donald A. Richardson, Plainsboro, N.J.

[73] Assignee: The UAB Research Foundation, Birmingham, Ala.

[*] Notice: This patent issued on a continued prosecution application filed under 37 CFR 1.53(d), and is subject to the twenty year patent term provisions of 35 U.S.C. 154(a)(2).

[21] Appl. No.: 08/621,232

[22] Filed: Mar. 25, 1996

[51] Int. Cl.⁶ .................................................. A61M 25/00
[52] U.S. Cl. .......................... 604/531; 604/532; 604/528; 604/526; 604/527; 604/95; 607/125; 600/373; 600/381
[58] Field of Search ................................ 604/93, 95, 264, 604/280, 281, 523, 524, 525, 526, 528, 530, 531, 532, 527; 607/122, 125; 128/642; 600/373, 381

[56] References Cited

U.S. PATENT DOCUMENTS

| | | |
|---|---|---|
| 3,890,977 | 6/1975 | Wilson . |
| 4,753,223 | 6/1988 | Bremer . |
| 4,919,133 | 4/1990 | Chiang . |
| 4,969,890 | 11/1990 | Sugita et al. . |
| 5,019,040 | 5/1991 | Itaoka et al. . |
| 5,055,101 | 10/1991 | McCoy ..................................... 604/281 |
| 5,069,226 | 12/1991 | Yamauchi et al. . |
| 5,089,005 | 2/1992 | Harada . |
| 5,120,308 | 6/1992 | Hess . |
| 5,192,301 | 3/1993 | Kamiya et al. . |
| 5,239,999 | 8/1993 | Imran . |
| 5,368,558 | 11/1994 | Nita . |
| 5,377,685 | 1/1995 | Kazi et al. . |
| 5,381,790 | 1/1995 | Kanesaka ............................... 607/125 |
| 5,383,923 | 1/1995 | Webster, Jr. . |
| 5,389,073 | 2/1995 | Imran . |
| 5,449,343 | 9/1995 | Samson et al. . |
| 5,465,717 | 11/1995 | Imran et al. . |
| 5,466,234 | 11/1995 | Loeb et al. . |
| 5,476,495 | 12/1995 | Kordis et al. . |
| 5,520,644 | 5/1996 | Imran ..................................... 604/281 |
| 5,531,664 | 7/1996 | Adachi et al. . |
| 5,588,964 | 12/1996 | Imran et al. ............................. 604/281 |
| 5,662,621 | 9/1997 | Lafontaine . |
| 5,697,380 | 12/1997 | Quiachon et al. . |
| 5,704,934 | 1/1998 | Neuwirth et al. . |
| 5,715,817 | 2/1998 | Steven-Wright et al. . |

FOREIGN PATENT DOCUMENTS

0 132 344   1/1985   European Pat. Off. .

*Primary Examiner*—Ronald K. Stright, Jr.
*Attorney, Agent, or Firm*—Gifford, Krass, Groh, Sprinkle, Anderson & Citkowski, P.C.

[57] ABSTRACT

A conformable catheter comprising a catheter handle, an elongated catheter tube, and a distal tip portion of the catheter tube, capable of assuming a desired pre-programmed shape. A wire member is disposed within the core of the catheter's tip portion and is formed of a material, such as, for example, a shape-memory binary nickel-titanium alloy, that will assume a pre-programmed shape after pre-shaping, heat treatment, cooling and subsequent heating. To pre-program the shape of the wire member, prior to assembly of the catheter, the wire member is wound around a shaped, heat resistant fixture, heated until the temperature of the wire member exceeds the temperature at which the shape of the wire member on the fixture becomes programmed into the wire member, and cooled. Upon subsequent heating of the wire member above its activation temperature after inclusion of the wire member into the catheter tubing, such as by controllably connecting the wire member to an electrical power source, the wire member, and thus the catheter's tip portion, assumes the pre-programmed curved or bent shape from its normally straight, generally linear disposition.

17 Claims, 4 Drawing Sheets

SHAPE MEMORY CATHETER

FIELD OF THE INVENTION

The present invention relates to vascular catheters for use in medical procedures and, more particularly, to catheters having distal ends, tips or segments that can be remotely shaped, guided or steered. The present invention also relates to methods of making such catheters.

BACKGROUND OF THE INVENTION

Catheters have been in common use in medical practice for many years. They are often used, for example, to probe locations inside a body of a patient which are otherwise unreachable without surgery. A catheter is first inserted into a vein, artery, or other structure or region of the body of the patient. The catheter is then guided to the area of concern by further inserting it into the patient's body. As medical knowledge increases, more uses of catheters have been developed and these uses have become more complex so that the ability to accurately and selectively steer and control the positioning and shape of the distal portion of the catheter has become of extreme importance. For example, there is a need to use steerable catheters to supply or remove fluids or cells to or from various internal tissues of the patient and to apply or sense electrical signals to or from such tissues. Administered fluids may, for example, be in the form of a liquid, suspension or gel containing a drug or other chemical used, for example, to treat or anesthetize the tissue.

In order to place the tip of the catheter in the correct location and position, it is often necessary or highly desirable to variously curve the catheter so that its distal portion will travel into the proper anatomical region or cavity as the catheter is inserted into the patient, or so that its distal portion conforms to the shape of the anatomical cavity so that the catheter's distal portion contacts the tissues of interest. After the distal portion has been so curved, it is also often desirable to rotate the catheter while maintaining the curvature of the distal region so that the intended portion of the catheter can then approach and/or contact the tissues of interest. It is also important that the catheter be able to make firm contact with the tissue of interest to facilitate reliable transmission or sensing of an electrical current to or from the tissue and/or reliable application or removal of fluid by the catheter.

A catheter which addresses some of the above problems is disclosed in U.S. Pat. No. 5,190,050, the entire disclosure of which is expressly incorporated by reference herein. In the catheter disclosed therein, the distal portion easily and reliably bends or twists in an angular orientation or curve that is selectively controllable. The distal end of the catheter is hollow and has at least two flat planar rigid juxtaposed shims mounted therein. The distal ends of the shims are attached to one another while the proximal end of at least one of the shims is attached to a pull cable and ultimately to the catheter handle. When a doctor or other user manipulates the catheter handle so that the catheter translates distally with respect to the handle, one of the shims follows the distal translation while the other shim retains its longitudinal distance from the handle causing the other shim and the associated distal portion of the catheter to longitudinally bend. Because of the planar shape of the shims and their rigidity, the bending of the distal portion of the catheter is always identical in direction, although varying in degree proportionally to the magnitude of the manipulation of the catheter handle, and is in a single plane of movement. The distal portion of the catheter can also optionally carry contact electrodes to transmit electrical pulses to or from tissue of the patient's body or can be made to pump fluids into or out of the body of the patient. Although the catheter disclosed in U.S. Pat. No. 5,190,050 is reliable, completely functional and useful for many applications, it is not able to assume a shape having a curvature in more than one plane.

There are certain internal passages or chambers in the body which are not easily accessible to a catheter that can bend in only one plane. In the heart, for example, when it is desired to apply electrical pulses to, detect electrical signals from, or to introduce or extract fluids to or from the mitral or tricuspid valve annulus, the tip of a catheter must be curved in two planes in order to properly contact the desired tissue. When the steerable catheter disclosed in U.S. Pat. No. 5,190,050 is used for this particular application, a doctor typically introduces the tip of the catheter into the heart's atrium and adjusts the catheter's handle to cause the tip to deflect in its single plane of deflection. The distal portion of the catheter's tip is then manipulated, either by rotation, by further insertion, or by a combination of both so that it contacts and is wedged against certain tissues and/or tissue walls within the heart. As a result, a proximal portion of the tip of the catheter, which does not contain the sandwiched juxtaposed rigid shims, is caused through such contact or abutment with tissue walls to assume a curve or bend in a plane that is different from the deflection plane of the distal end of the catheter's tip. As a result of this double twist in the catheter's tip, the catheter can then be further inserted so that it enters the mitral or tricuspid valve annulus. The second twist in the tip of the catheter, however, is not fixed or locked, is not readily controllable or selectively attainable, and is not pre-programmed into the catheter. As a consequence, the catheter tip manipulations needed to attain the desired catheter tip shape require substantial experience and skill.

The multiform twistable tip deflectable catheter disclosed in U.S. Pat. No. 5,358,479, the entire disclosure of which is expressly incorporated by reference herein, employs a single shim with at least one transverse or lateral twist which enables the tip of the catheter tube to assume a lockable pre-programed curvature in more than one plane. Although this catheter is also reliable, completely functional and useful for many applications, its twisted shim design places some limit on the particular shapes that the catheter tip can assume.

SUMMARY OF THE INVENTION

The conformable catheter of the present invention broadly comprises a catheter handle, an elongated catheter tube, and the distal tip portion of the catheter tube, which is capable of assuming a desired pre-programmed shape. The catheter tube, which is preferably a hollow, rigid, reinforced tube, is sufficiently long to be inserted into a patient to reach a body cavity of interest, such as the heart.

The catheter's tip portion is preferably made of a softer material so that it is more flexible than the catheter tube. A plurality of electrical contact plates or bands are mounted onto or around the outer surface of the catheter's tip portion. The electrical contact plate are connected to wires which pass through the entire length of the catheter tube and through the handle where they may be separately connected to a plug connectable to signal sensors or to an electrical power source. A wire member is disposed within the core of the catheter's tip portion, preferably extends through its entire length. The wire member is formed of a material that will assume a pre-programmed shape after pre-shaping and heat treatment and subsequent heating, such as a shape-memory binary nickel-titanium alloy (about 49.0 to about 50.7% titanium) or ternary nickel-titanium alloys containing other elements, such as chromium. Suitable shape-memory alloys include those commercially known as "nickel-titanium", "titanium-nickel", "Tee-nee", "Memorite", "Nitinol", "Tinel" and "Flexon". The wire member is preferably electrically connected by one or more wires extending through the catheter tube and the handle to another plug which is connectable to an electrical power supply and optionally a microprocessor.

A plurality of buttons mounted to the handle are employed by the user to control heating of the wire member or connection of the electrical contact plates, or both. Some of the buttons may be rheostatically controlled such that the amount of electrical power flowing in the circuit controlled by the button is adjustable.

To pre-program the shape of the wire member, prior to assembly of the catheter, the wire member is wound around a shaped, heat resistant fixture. A groove is formed in the outer surface of the fixture, sized and shaped so that the wire to become the wire member can be mounted therein. After winding the wire member around the fixture, the wire member is secured in place. To control heat treatment of the wire member, the fixture may then be mounted within a heat sink shell. By varying the composition of the wire member, the duration of heat treating, the temperature of the oven, and the configurations of the heat sink shell, or even by eliminating the heat sink entirely, the activation properties of the wire member may be varied, i.e., the temperature at which the portions of the wire member assume their pre-programmed shape. The assembly is then placed in a pre-heated oven and heated for a predetermined time. Heating of the wire member is continued until the temperature of the wire member exceeds the temperature at which the shape of the wire member on the fixture becomes programmed into the wire member. The entire assembly is then cooled and the wire member is unwound from the fixture and straightened. Preferably, at least one electrically conducting wire is then attached to the wire member, although more than one wire may be attached to the wire member at various points. The wire member is then preferably attached to a stainless steel spring, wrapped in a heat shrink electrical and thermal insulation sheath, and inserted into central lumen of the catheter so that the wire member is located at the catheter's tip.

In operation, after the catheter's distal tip portion is inserted into the desired point in the body or vessel at which the catheter is to be used, the wire member is activated by heating it electrically thereby causing the catheter's tip portion to assume the pre-programmed curved or bent shape from its normally straight, generally linear disposition. Activation is preferably accomplished by connection of electric power to the wire member by activation of one of the buttons on the catheter handle. The electrical power causes the temperature of the wire member to rise so that it transfigures to a substantially rigid contoured condition, assuming substantially the same shape that it had during heat treatment when it was wrapped around the fixture. Various pre-programmed shapes can be selected to conform to various body cavities, such as, for example, a conical spiral to substantially conform to the heart's left ventricle and an egg-shaped spiral to conform to the shape of the right atrium of the heart.

Upon electrical deactivation of the catheter's tip portion, the temperature of the wire member decreases and, at the same time its rigidity decreases so that the catheter's tip portion may conform and contact the walls of the body cavity being examined or treated with the catheter.

The shape of the tip portion of the catheter is thus electrically controlled, allowing it to assume its pre-programmed shape or to become deformable or limp simply by appropriate connection or disconnection of the electrical power.

By having different segments of the wire member individually controllable, i.e., by connection of more than one wire at different segments of the wire member, the user can activate different segments thereof at different times or rates. A rheostat control may be used to activate the wire member at any rate desired.

The wire member may be heated by applying an electrical signal thereto or alternatively, since the wire member will assume its pre-programmed shape merely upon heating, by heating the catheter's tip portion in other ways, such as, for example, by using a laser that may or may not form a part of the catheter's tip, non-invasive microwave heating of the catheter's tip, or heating of the catheter's tip by infusing heated fluid either through the catheter or from a source separate from the catheter.

The catheter's tip is thus able to assume a three-dimensional shape to contact tissues at a variety of discrete locations within a body cavity. Each of the electrical contact plates on the catheter's tip may be individually controlled so that each can be positioned to contact different tissues. Consequently, the electrical measurements taken may be used to generate a three-dimensional image of the electrical properties of the tissue being examined, thereby aiding medical diagnosis.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

BRIEF DESCRIPTION OF THE DRAWINGS

In the drawings, wherein like reference numerals delineate similar elements throughout the several views.

DETAILED DESCRIPTION OF THE PRESENTLY PREFERRED EMBODIMENTS

Figure 1:
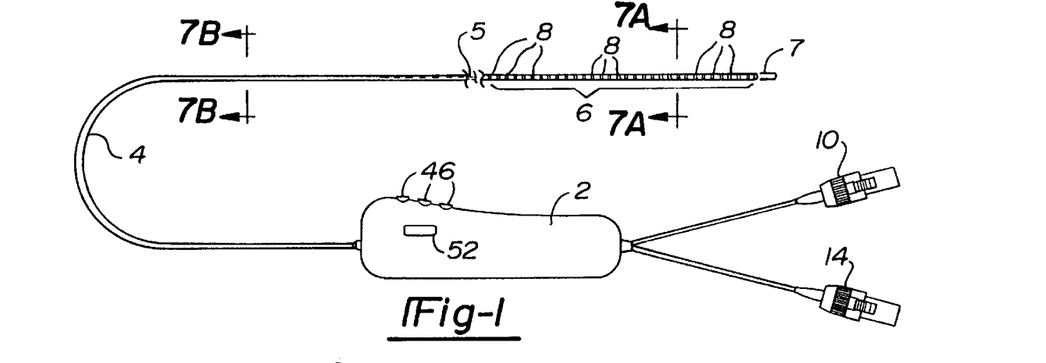
FIG. 1 is a side view of one embodiment of the conformal catheter of the present invention in an inactivated state.
Figures 2A, 2B, 3A, 3B:
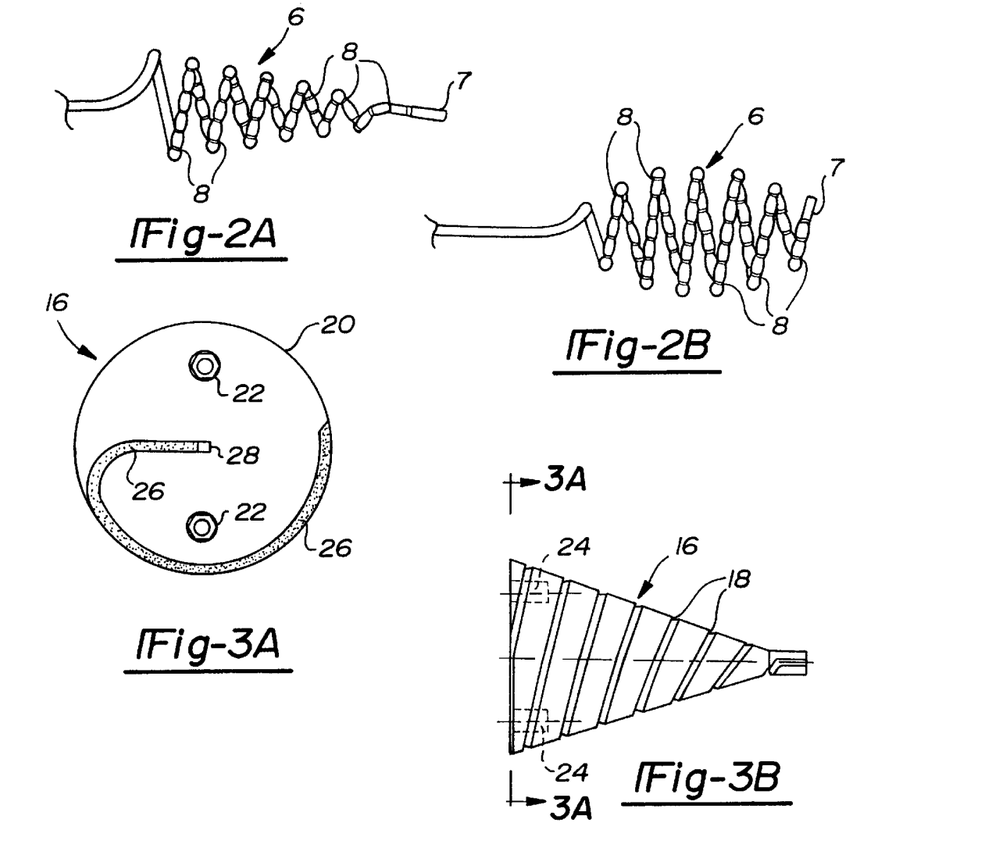
FIGS. 2A and 2B are side views of two exemplary shapes of the distal tip portion of the conformal catheter of the present invention in an activated state.
FIGS. 3A and 3B are end and side views, respectively, of one embodiment of a fixture used in pre-programming the shape of the wire member of the conformal catheter of the present invention.

As shown in FIG. 1, the conformable catheter of the present invention broadly comprises a catheter handle 2, an elongated catheter tube 4, and the distal tip portion 6 of the catheter tube 4. The distal tip portion 6 of the catheter tube 4, is the portion of the catheter that assumes a pre-programmed shape as desired, as shown in FIGS. 2A and 2B.

Referring now to FIG. 1, the catheter tube 4 has a length sufficient for it to be inserted into a patient's body lumen or cavity or the like so that the deflectable distal tip portion 6 of the catheter tube 4 can be controllably directed to and reach a particular point or location within the patient's body—as for example a location within the vascular system, such as the heart.

The catheter tube 4 is a hollow tube formed of a rigid or stiff material, preferably and by way of example a nylon co-polymer such as "PEBAX" resin manufactured by ATOChem. The catheter tube 4 may also be comprised of any suitable plastic material such as PVC or a polyurethane, and preferably has an outer diameter of about 2 French to about 11 French, and a length of about 20 to 80 inches. In order to give the catheter tube 4 substantial effective rigidity and strength, it is preferred to include a wire braid 5 embedded into the catheter tube 4, although the wire braid may be eliminated and, instead or in addition, a material of high durometer used. The wire braid is preferably comprised of about 12 to 16 steel wires that are interwoven along the length of the catheter tube 4. The wire braid may, alternatively, be comprised of more or less than 12 to 16 wires, and the wires may, alternatively, be formed of a material other than steel such, illustratively, as fiberglass. The nylon co-polymer and wire braid strengthen and support the structure of the catheter tube 4 and are effective to transmit a torque applied to the handle 2 by a user to the catheter's tip portion 6.

The catheter's tip portion 6 is preferably comprised of a relatively lower durometer or "softer" material to increase its flexibility, so long as such material admits of firm attachment to the remainder of the catheter tube 4. In addition, it is preferred that the distal tip portion 6 not include an interior wire braid, thereby facilitating its selective bendability or deflection under a user's control.

Figure 7A:
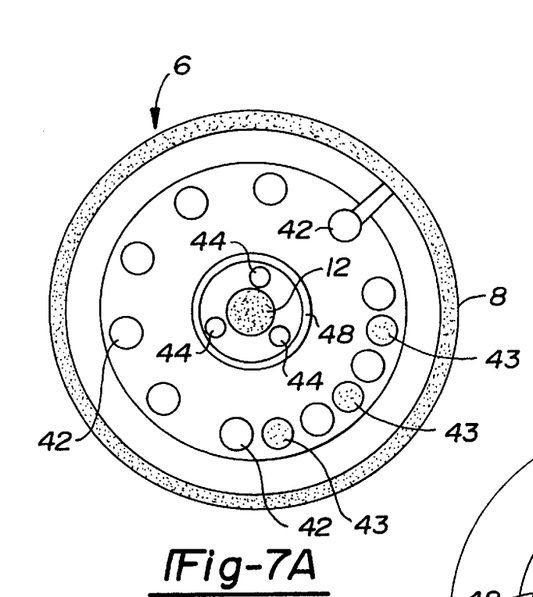
FIGS. 7A and 7B are cross-sectional drawings of the conformal catheter of the present invention taken along lines 7A—7A and 7B—7B in FIG. 1.
Figure 7B:
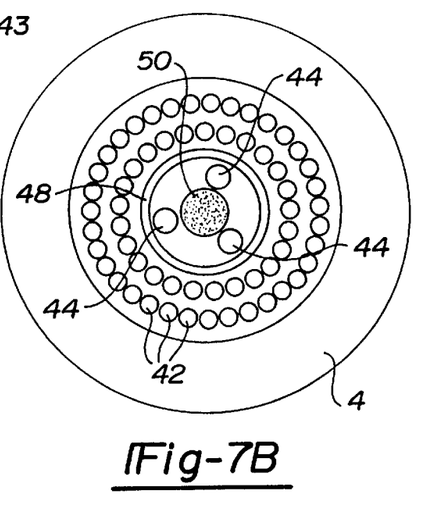

One or more electrical contact plates 8 are integrally mounted onto the outer surface of the catheter's tip portion 6. These contact plates 8 may be bands, as shown in FIG. 1, that each wrap around the circumference of the catheter's tip portion 6 and are made of electrically conducting material, such as for example platinum, gold or silver. Preferably, such bands are about 0.50 to about 5.0 mm in width. During one preferred assembly process, each band is electrically connected to an electrically conducting sensor wire 42, as shown in FIG. 7A. Each sensor wire 42 is threaded through a hole in the catheter's tip portion 6 and then each band contact plate 8 is slid into position over the catheter's tip portion 6. The sensor wires 42 connected to the contact plates 8 pass through the entire length of the catheter tube 4, as shown in FIG. 7B, and through the handle 2 where they may be separately connected to a plug 10, shown in FIG. 1, that is connectable to signal sensors (not shown) or to an electrical power source (not shown) that is operable to selectively sense or provide electrical pulses or signals from or to one or more of the wires and thus one or more of the contact plates 8. The contact plates 8 may alternatively be formed as buttons or other geometric shapes of less than about 1 mm. in diameter that are fixedly embedded into the material forming the catheter's tip portion 6 and electrically connected to the wires 42 that terminate at the handle plug 10. One such electrical contact plate 8 may also be disposed at the distal tip of the catheter's tip portion 6, as shown in FIG. 1.

A wire member 12 is disposed within the core of the catheter's tip portion 6 and preferably extends through the entire length of the tip portion 6, i.e., the portion of the catheter tube 4 that is to assume a desired curve. The wire member 12 is formed of a material that will assume a pre-programmed shape after pre-shaping and heat treatment as discussed in detail below and upon being heated, such as by the application of electrical power thereto. The wire member 12 is preferably formed of a wire of a shape-memory binary nickel-titanium alloy (about 49.0 to about 50.7% titanium) with a diameter of greater than about 0.003 inches, but preferably less than about 0.020 inches. Other wire diameters may be used depending upon the inner diameters of the body passages through which the catheter is intended to travel. The wire member may also be formed of shape-memory ternary nickel-titanium alloys containing other elements, such as chromium. Suitable shape-memory alloys include those commercially known as "nickel-titanium", "titanium-nickel", "Tee-nee", "Memorite", "Nitinol", "Tinel" and "Flexon". The wire member 12 is preferably electrically connected by one or more electrically conducting activator wires 44 extending through the catheter tube and the handle 2 to another plug 14, which is connectable to an electrical power supply and optionally a microprocessor. The microprocessor may be used to program and control the electrical signals provided by the electrical power supply.

A plurality of user actuatable buttons 46 are mounted to the handle 2 and are electrically connected to a source of power so that the user can control the electrical power applied to the wire member 12 through activator wires 44, to the electrical contact plates 8 through sensor wires 42, or to both. Preferably, at least some of the buttons 46 are rheostatically controlled by a sliding rheostat 52 button such that upon depression of a button 46, sliding of the rheostat allows increased electrical power to flow in the circuit controlled by the button 46 that has been depressed. The number of buttons 46 is selected to provide the user with the desired control of the various catheter functions. For example, a plurality of buttons can control various ones of the electrical contact plates and/or a plurality of buttons can control electric power applied to various portions of the wire member 12, as discussed in detail below.

To pre-program the shape of the wire member 12, prior to assembly of the catheter, the wire member 12 is wound around a wire form or fixture 16, one exemplary embodiment of which is shown in FIGS. 3A and 3B. The fixture 16 is formed of a material that retains it shape above the temperature used to pre-program the wire member, as discussed below. Preferably, the fixture 16 is made from an aluminum block that is machined and/or molded to the desired shape and configuration. For example, in FIG. 3B, the fixture 16 is in the shape of a cone, although other shapes for the fixture 16 may be selected to result in any desired pre-programmed catheter tip configuration. A groove 18 is formed in the outer surface of the fixture 16 and is sized and shaped so that the wire to become the wire member 12 can be mounted therein. As shown in FIG. 3A, an end plate 20 is attachable to the end of the fixture 16 by screws (not shown) which pass through holes 22 in the plate 20 into corresponding bores 24 in the fixture 16. The end plate 20 also has a groove 26 formed therein sized and shaped for mounting the wire member 12 therein so that a gradual pre-formed curve can be formed at the proximal end of the wire member 12, i.e., toward the left in FIG. 3B. The end plate 20 has a central hole 28 through which the wire member 12 can pass when it is mounted to the fixture 16.

Figures 4A, 4B:
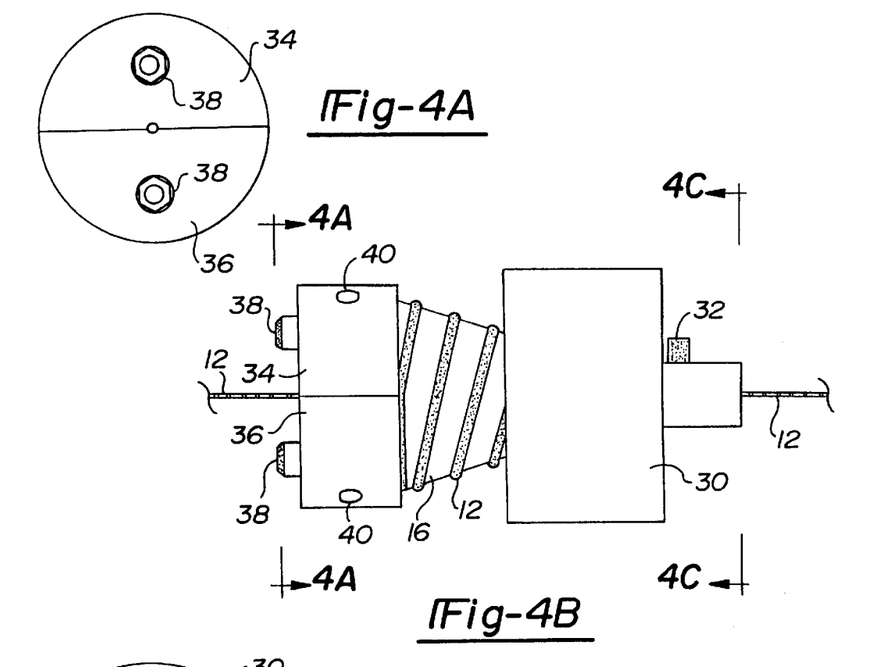
FIGS. 4A, 4B and 4C are end, side and end views, respectively, of an exemplary assembly used in heat-treating the wire member of the conformal catheter of the present invention.
Figure 4C:
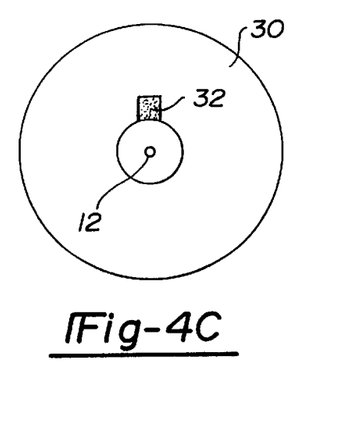

After the wire member 12 is wound around and mounted in grooves 18, 26 of the assembled fixture 16, 20, a two-piece split holder 34, 36 is preferably assembled around the fixture 16 and attached to the fixture 16 by a pair of locking pins 40 and a pair of mounting screws 38, as shown in FIGS. 4A and 4B. The split holder 34, 36 assures that the wire member 12 remains wrapped tightly around the fixture 16 during subsequent heat treatment. To control heat treatment of the wire member 12, the fixture 16 may then be mounted within a heat sink shell 30, one exemplary embodiment of which is shown in FIGS. 4B and 4C, and secured thereto by a set screw 32. The heat sink shell 30, and split holder 34, 36 are preferably made of aluminum, although other metals and materials, such as ceramics, may be used. Other configurations of heat sink assemblies may be used depending on the shape of the fixture 16 and upon the particular electrical activation properties of the wire member 12 that are required for a particular catheter application, including the catheter's intended treatment or data acquiring location within a patient. The entire assembly, including the heat sink shell 30, containing the wire member 12 wrapped around the fixture 16, and the split holder 34, 36 is then placed in a preheated oven and heated for a predetermined time. Preferably, the oven is at a temperature of about 480° C. to about 500° C. and heat treatment of the assembly is continued for about 2 to about 30 minutes, at which time the assembly is removed from the oven and cooled. The heat sink 30, and split holder 34, 36 are employed to control the temperature that various parts of the wire member 12 reach during the heat treatment process. Thus, a thick heat sink allows the wire member 12 to heat up more slowly then if the wire member 12 is uncovered and does not permit the wire member 12 to reach the oven temperature if the assembly is removed from the oven in a sufficiently short time. Such controlled heating of the Wire member 12 controls the temperature that various portions of the wire member 12 activates. Alternatively, no heat sink shell 30 may be used; accordingly, all parts of the wire member 12 after heat treatment will activate at the same temperature. Heating of the wire member is thus continued until the temperature of the wire member 12 exceeds the temperature of the wire member 12 at which the shape of the wire member 12 on the fixture 16 becomes programmed into the wire member 12, as discussed in detail below. Preferably, cooling is accomplished rapidly by quenching the entire assembly in a cold water bath. Alternatively, the assembly may be cooled gradually by placing it in rock salt at room temperature. The heat treating assembly is then dismantled, and the wire member 12 is unwound from the fixture 16 and straightened. Preferably, at least one electrically conducting activator wire 44 is then attached to the wire member 12, such as by soldering with silver solder. Although only one electrically conducting activator wire 44 may be used, soldered to either the proximal or distal end of the wire member 12 or at some point in between, preferably more than one electrically conducting activator wire 44 is soldered to the wire member 12, most preferably three: one connected near the distal end of the wire member 12, one near its proximal end, and one at the middle. The wire member 12 is then preferably fixedly attached to a stainless steel wire or spring 50 and wrapped in a heat shrink insulation sheath 48 to isolate the wire member 12 and the conducting activator wires 44 both electrically and thermally from the other elements in the catheter's tip portion 6 and in the remainder of the catheter 4. The electrically conducting sensor wires 42 connected to the electrical contact plates 8 are arrayed circumferentially on the surface of the central lumen of the catheter and the entire assembly, wrapped in the insulation sheath 48, is then inserted into central lumen of the catheter. The spring 50 provides columnar strength to the catheter tube 4 so that torque applied to the handle by a user will be translated to a torque at the catheter's tip. The electrically conducting wires 44, 42 are then connected to one of the plugs 10, 14, or alternatively to one of the buttons 46 and/or the rheostat control 52.

Figure 5A:
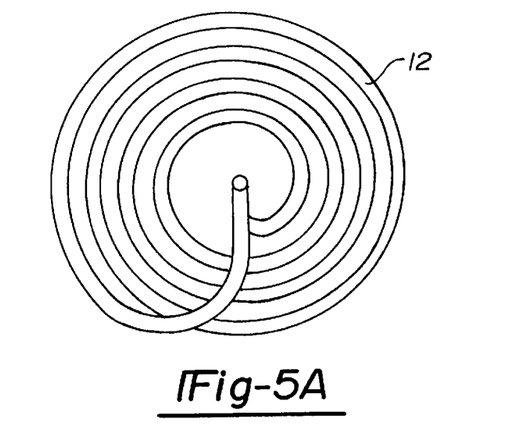
FIGS. 5A and 5B are end and side views, respectively, of the wire member of the conformal catheter of the present invention in an activated state.
Figure 5B:
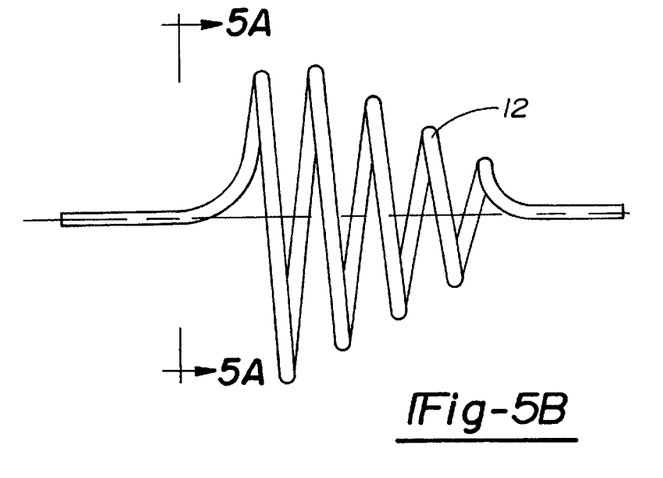
Figure 6:
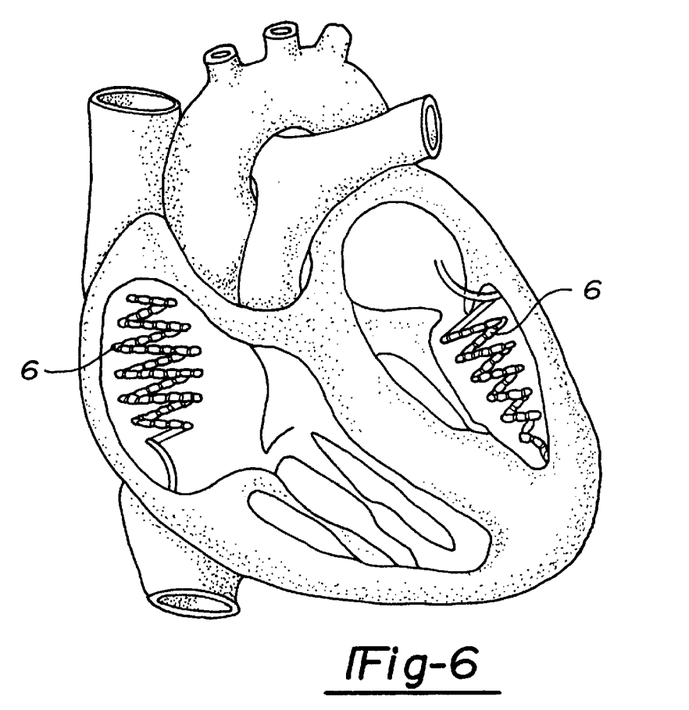
FIG. 6 is sectional drawing of a human heart having two conformal catheters of the present invention placed therein.

In operation, the catheter's distal tip portion 6 is first inserted into, for example, a patient. The location of the catheter's distal tip portion 6 within the patient is typically monitored non-invasively as, for example, through the use of fluoroscopy, X-rays or sonography or the like. When the distal tip portion 6 of the catheter tube 4 reaches the desired point in the body or vessel at which the catheter is to be used, the distal tip portion 6 can be selectively, remotely activated to assume the pre-programmed curved or bent shape, as shown in FIGS. 2A and 2B, from its normally straight, generally linear disposition. Activation of the catheter's tip portion is accomplished by connection of electric power to the wire member 12 by activation of one of the buttons 46 on the catheter handle 2. When electrical power is connected to the wire member 12, the temperature of the wire member 12 rises, and the wire member 12 transfigures from its substantially readily deformable condition to a substantially rigid contoured condition, assuming substantially the same shape that it had during heat treatment when it was wrapped around the fixture 16. Shown in FIGS. 5A and 5B are end and side views, respectively, of the wire member 12 formed using the cone-shaped fixture 16 shown in FIGS. 3A and 3B in its activated configuration. Thus, if the catheter's tip portion 6 is positioned within the heart of a patient upon activation, as shown in FIG. 6, the catheter's tip portion 6 curls into its pre-programmed shape which corresponds substantially to the shape of the fixture 16 used in heat treating the wire member 12. As can be seen in the right portion of FIG. 6, the pre-programmed conical spiral of the catheter's tip portion 6 substantially conforms to the heart's left ventricle. Additionally, the straightened tip segment, which can also be seen in FIG. 2A, is shaped so that it anchors in the apex of the heart's ventricle. By changing the shape of the fixture 16 used in heat treating the wire member, other pre-programmed shapes for the catheter's tip portion can be obtained upon activation of the catheter's tip portion. For example, an egg-shaped spiral catheter tip can be obtained by using a egg-shaped fixture 16 during heat treatment of the wire member 12. Such an egg-shaped spiral catheter tip, as shown in FIG. 2B, is particularly useful to conform to the shape of the right atrium of the heart, as shown in the left portion of FIG. 6. Other catheter tip configurations can be pre-programmed to conform to other body cavities with different shapes and sizes or to press against one or more walls of such body cavities.

In use, it is often desirable to selectively rotate the entire catheter tube 4 through a desired angular adjustment after a desired curve in the distal tip portion 6 has been attained. Such a rotation may be readily and reliably achieved by selectively rotating the entire handle 2 about its longitudinal axis. The preferred rigidity and stability of the material and structure comprising the catheter tube 4 and the supporting structure of the spring 50 allow such axial rotation of the handle 2 to be smoothly, directly and reliably transmitted to the catheter's distal tip portion 6 with little risk of unintended or unanticipated sudden rotational movements or jolts.

Upon electrical deactivation of the catheter's tip portion 6, i.e., disconnecting the wire member 12 from the electrical power source, the temperature of the wire member 12 decreases and, at the same time its rigidity decreases so that the catheter's tip portion 6 may conform and contact the walls of the body cavity being examined or treated with the catheter.

Since the curvature of the catheter's tip portion 6 is electrically controlled, the tip portion 6 can assume its pre-programmed shape or allowed to become deformable or limp simply by appropriate connection and disconnection of the electrical power applied to the wire member 12. The catheter's tip portion 6 may be activated and deactivated, either completely or partially, as often as desired simply by connection and disconnection, either completely or partially, of the wire member 12 from the power source.

By having different segments of the wire member 12 individually controllable, i.e., by having separate activator wires 44 connected to different portions of the wire member 12, the user is able to activate different portions of the wire member 12 at different times or rates. Thus, by pressing the appropriate buttons 46 on the catheter handle 2, the distal most portion of the wire member 12 may be activated first so that it begins to assume its pre-programmed shape first, and the proximal end of the wire member of the wire member may be activated last by depressing the button that activates that end last. Alternatively, one button 46 may be used to activate all sections of the wire member 12 at the same time. When a rheostat control 52 is used, the user can activate the wire member 12 at any rate desired.

In heat treating the wire member 12 it is preferred to use a high temperature heating oven, other conventional methods of pre-treating the wire member by heating may be used. By appropriately varying the shape and thickness of the heat sink shell 30, the manner in which the wire member 12 assumes it pre-programmed shape may be adjusted since the shape and thickness of the heat sink shell determines how quickly and to what extent the wire member is heated in the heat treatment process. Thus, by appropriately sizing and shaping the heat sink 30 during the pre-treating process, activation by electrical connection of the wire member 12 at one point will result in one end of the wire member 12 beginning to curve at a faster rate than other portions of the wire member 12, or alternatively so that the entire wire member curves at the same rate. In addition, by varying the temperature of the oven and the duration of heat treatment, the particular temperature at which the wire member 12 activates by resistive heating upon the application of electrical power can be adjusted. Using the heat treating parameters discussed above will result in the wire member activating at a temperature of about 42° C. to about 52° C. Varying the heat treatment temperature and/or using ternary nickel-titanium alloys will vary the activation temperature of the wire member.

The electrical power that is applied to the wire member 12 may take any forms, such as, for example, a steady, constant amplitude signal, a single pulse signal, a signal comprising a series of periodic pulses, a wave signal, a ramp signal, or any combination of these signals. Alternatively, since the wire member 12 will assume its pre-programmed shape merely upon heating, the wire member 12 may be heated by heating the catheter's tip portion in other ways, such as, for example, by using a laser that may or may not form a part of the catheter's tip, non-invasive microwave heating of the catheter's tip, or heating of the catheter's tip by infusing heated fluid either through the catheter or from a source separate from the catheter.

In addition, in order to precisely monitor the temperature of the wire member 12 and/or the catheter's tip portion 6, a thermocouple 7 may be included in the catheter's tip portion which is electrically connected to a temperature display device mounted to the catheter handle 2 or elsewhere.

Because the catheter's tip is able to assume a three-dimensional shape thereby making contact with tissues at a variety of discrete locations within a body cavity, and because the catheter's tip may include numerous individually controlled electrical contact plates 8, each contact plate 8 can be positioned to contact different tissues. Consequently, the electrical measurements taken of the tissues may be used to generate a three-dimensional image or display of the electrical properties of the tissue being examined, thereby aiding medical diagnosis.

Although the catheter of the present invention is expressly disclosed for use in sensing electrical signals in body tissues and/or for applying electric power to such tissues, if this feature is not desired, the catheter design may be readily and suitably modified by eliminating the electrical contact plates 8 in the catheter's tip portion 6, the electrical sensor wires 42 and the electrical power source or sensor. Similarly, optical fibers 43 can be provided instead of, or in addition to, the electrical sensor wires 42. In such a modified embodiment one or more optical fibers may be connected to a light source, such as a laser, while one or more other optical fibers are connected to a video camera, light sensor and/or similar viewing or recording devices. Also, a tube may extend through the length of the catheter tube 4, 6 for removal of patient tissue or fluids or for supplying fluids to the patient's tissues of body cavities or organs. Any one or more of these alternative utilities or embodiments may also be combined one with another for a particular use that is contemplated or intended for the catheter of the present invention.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A positionable, shapable catheter comprising:
   a catheter handle;
   an elongated catheter tube having longitudinally spaced apart proximal and distal ends, said proximal end of said catheter tube being fixedly attached to said catheter handle, said distal end comprising an elongated conformable portion;
   a single wire member disposed within said catheter distal portion, said single wire member being comprised of a shape-memory material and having a plurality of independently controllable longitudinally adjacent sections capable of transfiguration of said catheter conformable portion; and
   a plurality of activator wires, each of said activator wires separately electrically connected to a different segment of said wire member, each extending through said catheter tube and each being connected to a source of electrical power, whereby upon heating of at least a portion of said wire member above an activation temperature, said at least a portion of said wire member transfigures from a substantially readily deformable condition to a substantially rigid activated contoured condition to conform to a body cavity, said activated contoured condition and said activation temperature being determined during pre-treating of said wire member.

2. The catheter of claim 1 and further comprising a strength-imparting material embedded into said catheter tube.

3. The catheter of claim 2 wherein said strength-imparting material comprises a wire braid.

4. The catheter of claim 3 wherein said strength-imparting material is selected from the group consisting of steel and fiberglass.

5. The catheter of claim 1 and further comprising a plurality of user actuatable buttons mounted to said handle.

6. The catheter of claim 5 wherein said buttons are capable of separately controlling the electrical power applied to said different segments of said wire member.

7. The catheter of claim 1, further comprising a control means for controlling electrical power supplied through said activator wires to said wire member.

8. The catheter of claim 1, further comprising an electrical contact plate mounted to an outer surface of said catheter distal portion, and an electrically conducting sensor wire electrically connected to the electrical contact plate and extending through said catheter tube.

9. The catheter of claim 1, wherein the activated contoured condition is a conical spiral.

10. The catheter of claim 1, wherein the activated contoured condition is an egg-shaped spiral.

11. The catheter of claim 1 wherein said catheter tube comprises a material selected from the group consisting of plastics, PVC, polyurethanes, and nylons.

12. The catheter of claim 1 wherein said distal end is comprised of a material of less rigidity than said proximal end.

13. The catheter of claim 1 wherein said wire member comprises a material selected from the group consisting of nickel-titanium alloys, nickel-titanium, titanium-nickel, Tee-nee, Memorite, Nitinol, Tinel, and Flexon.

14. The catheter of claim 1, wherein said activated contoured condition is a three-dimensional shape.

15. The catheter of claim 1 wherein said source of electrical power comprises a signal selected from the group consisting of constant amplitude, single pulse, periodic pulse, wave, ramp, and combinations thereof.

16. The catheter of claim 1 and further comprising a thermocouple located in said catheter distal portion, said thermocouple electrically connected to a temperature display.

17. The catheter of claim 1 and further comprising optical fibers provided on of said catheter.

* * * * *

UNITED STATES PATENT AND TRADEMARK OFFICE
CERTIFICATE OF CORRECTION

PATENT NO. : 5,997,526
DATED : December 7, 1999
INVENTOR(S) : Jeffrey J. Giba et al.

It is certified that error appears in the above-indentified patent and that said Letters Patent is hereby corrected as shown below:

Column 2, line 65 - Insert --and-- before "preferably".
Column 3, line 44 - Insert --the-- before "central".
Column 5, line 35 - Replace "admits of" with --permits--.

Signed and Sealed this

Twentieth Day of March, 2001

Attest:

NICHOLAS P. GODICI

*Attesting Officer*  *Acting Director of the United States Patent and Trademark Office*